United States Patent
Dovertie

(10) Patent No.: US 8,013,207 B2
(45) Date of Patent: Sep. 6, 2011

(54) APPARATUS AND METHOD OF FORMING A COMPOSITE WEB STRUCTURE AND AN ABSORBENT STRUCTURE COMPRISING SAID WEB

(75) Inventor: Ralph Dovertie, Västra Frölunda (SE)

(73) Assignee: SCA Hygiene Products AB, Gothenburg (SE)

(*) Notice: Subject to any disclaimer, the term of this patent is extended or adjusted under 35 U.S.C. 154(b) by 1538 days.

(21) Appl. No.: 10/905,161

(22) Filed: Dec. 18, 2004

(65) Prior Publication Data
US 2006/0135922 A1 Jun. 22, 2006

Related U.S. Application Data

(60) Provisional application No. 60/530,997, filed on Dec. 22, 2003.

(51) Int. Cl.
*A61F 13/15* (2006.01)
*B27N 1/00* (2006.01)
*B29C 43/22* (2006.01)

(52) U.S. Cl. ............... 604/367; 604/378; 604/385.101; 264/517; 264/518

(58) Field of Classification Search ............... 264/518, 264/510, 112, 113; 604/367, 368, 378, 385.101
See application file for complete search history.

(56) References Cited

U.S. PATENT DOCUMENTS

| | | | |
|---|---|---|---|
| 3,128,018 A | 4/1964 | Corsette et al. | |
| 3,518,726 A | 7/1970 | Banks et al. | |
| 4,551,191 A | 11/1985 | Kock et al. | |
| 4,765,780 A | 8/1988 | Angstadt | |
| 5,044,052 A | 9/1991 | Hertel et al. | |
| 5,213,817 A | 5/1993 | Pelley | |
| 5,429,788 A | 7/1995 | Ribble et al. | |
| 5,614,147 A * | 3/1997 | Pelley ................ | 264/518 |

(Continued)

FOREIGN PATENT DOCUMENTS

EP 0 783 877 7/1997

(Continued)

OTHER PUBLICATIONS

International Preliminary Examination Report issued Jun. 7, 2006 in corresponding PCT/SE2004/001944.

(Continued)

*Primary Examiner* — Jacqueline F Stephens
(74) *Attorney, Agent, or Firm* — Buchanan Ingersoll & Rooney PC

(57) ABSTRACT

A method and a device of forming a composite web containing at least one layer of superabsorbent particulate material and at least one layer of fibrous material, the web being intended for use as an absorbent structure in absorbent articles. The layers of fibrous material and at least one layer of particulate material are deposited in consecutive steps on a moving foraminous support (12), wherein the airborn stream of particulate material when entering an applicator chamber (15) is allowed to expand and is forced to change flow direction at an angle between about 90 and about 125°, preferably between 100 and 120°, with respect to the first flow direction, resulting in a considerable reduction of speed of the stream of particulate material as it exits the outlet opening (19) of the applicator chamber (15). The invention further refers to an absorbent structure has a composite web made according to the method and includes at least one discrete layer (22*a,b*) of superabsorbent particles arranged between discrete layers (19*a-c*) of fibrous material.

22 Claims, 4 Drawing Sheets

U.S. PATENT DOCUMENTS

| | | |
|---|---|---|
| 5,885,516 A | 3/1999 | Christensen |
| 2003/0143324 A1 | 7/2003 | Delzer et al. |

FOREIGN PATENT DOCUMENTS

| | | |
|---|---|---|
| EP | 1 035 818 B1 | 4/2002 |
| EP | 1 253 231 A2 | 10/2002 |
| EP | 1 253 231 A3 | 1/2003 |
| JP | H02-107250 | 4/1990 |
| JP | H9-187476 | 7/1997 |
| JP | H11-285513 | 10/1999 |
| JP | 2001-171029 | 6/2001 |
| WO | WO 92/19198 A1 | 11/1992 |
| WO | WO 2004/084784 A1 | 10/2004 |

OTHER PUBLICATIONS

English language translation of Japanese Official Action issued in corresponding Japanese application No. 2006-545298.

* cited by examiner

APPARATUS AND METHOD OF FORMING A COMPOSITE WEB STRUCTURE AND AN ABSORBENT STRUCTURE COMPRISING SAID WEB

CROSS-REFERENCE TO RELATED APPLICATIONS

The present application claims the benefit of U.S. Provisional Application No. 60/530,997, filed in the United States on Dec. 22, 2003, the entire contents of which are hereby incorporated herein by reference.

FIELD OF THE INVENTION

The present invention relates to a method of forming a composite web containing at least one layer of particulate material and at least one layer of fibrous material, said web being intended for use as an absorbent structure in absorbent articles, such as diapers, pant diapers, incontinence products, sanitary napkins and the like, wherein at least one layer of fibrous material and at least one layer of particulate material are deposited in consecutive steps on a moving foraminous support to form layers on top of each other. The invention further refers to a device for making the composite web and an absorbent structure comprising the composite web.

BACKGROUND OF THE INVENTION

Absorbent articles such as diapers, incontinence guards, sanitary napkins, intended to be disposed after one single use, contain an absorbent structure having the capability to acquire large amounts of liquid under a short period of time, having further the ability to distribute the liquid and to store the liquid. This means that the absorbent structure usually comprises several different layers having different properties with respect to each other. It is further desired that such absorbent articles are thin and discrete to wear.

Frequently, the absorbent structure comprises at least a liquid acquisition layer and a liquid storage layer. The liquid storage layer often comprises a composite web structure of fibrous material, usually cellulosic fluff pulp, and particulate superabsorbent material, which is a polymer having the ability to absorb water or bodily fluids many times its own weight. The superabsorbent material is either mixed with the fibrous material or applied in a layered configuration between fibrous layers. The liquid acquisition layer often comprises a porous fibrous layer of wet resilient fibers, such as synthetic fibers, or polymeric foam materials.

Cellulosic fluff pulp of different types are available, such as mechanical, thermomechanical, chemithermomechanical or chemical pulp. Fluff pulp is delivered in bales or rolls and is defibrated in pulp mills before being formed. Mat forming for forming absorbent structures is carried out by transporting the defibrated pulp from the pulp mill in an air flow to a forming unit, usually in the form of what is known as a mat-forming wheel. This is air-permeable and the fibers remain on the periphery of the mat-forming wheel and forms a fiber mat of a low density, which is subsequently compressed.

During mat forming, a continuous web can be formed, which is subsequently compressed and cut to individual absorbent structures adapted to be applied in an absorbent article. Alternatively the mat-forming wheel is provided with a plurality of moulds arranged over the periphery of the wheel so that a plurality of individual absorbent structures of a desired shape and size are formed directly on the mat-forming wheel.

The prior art teaches different types of mat-forming wheels for making absorbent structures. U.S. Pat. No. 3,518,726 discloses mat-forming in moulds, wherein the air flow and the forming in the moulds is controlled by the bottom of the moulds having different hole density and/or different hole size in different areas.

U.S. Pat. No. 4,765,780 discloses that fibers are fed in individual fiber streams to different forming hoods along the periphery of a large mat-forming wheel. Different layers are formed on top of each other as the forming wheel passes the different forming hoods. Superabsorbent particulate material may be added to one of these fiber streams.

In EP-A-1 253 231 there is disclosed a method of forming a fibrous web wherein separate air flows containing fibers are supplied to a number of different mat-forming wheels. Separate web layers are formed on the respective mat-forming wheel and are combined downstreams of the mat-forming wheels to form a common fibrous web, which is subsequently compressed. Superabsorbent particles may be added together with the fibrous streams or separately. The process is told to result in an increased manufacturing quality of the fibrous web formed and an increased manufacturing speed.

The prior art further teaches different methods and devices for applying particulate superabsorbent material in a fibrous web either in a mixed or layered configuration.

U.S. Pat. No. 5,885,516 discloses a method and an apparatus for introducing a superabsorbent powder at an intermediate stage between an initial supply of fibers and the final formation of the composite web. The superabsorbent powder is applied to the fibrous web by spreading the powder by means of a rotating brush cylinder, a perforated compressed air pipe or a pair of rod electrodes.

U.S. Pat. No. 5,429,788 discloses an apparatus and a method for forming a discrete layer of superabsorbent particulate material within a composite web. The particulate material is conveyed by gravity or in a conveying gas stream into a forming chamber. A depositing mechanism is located within the forming chamber to selectively dispense the particulate material in a fibrous web supported by a foraminous conveyor.

U.S. Pat. No. 5,213,817 discloses an apparatus for intermittently applying particulate superabsorbent material on a moving fibrous substrate. The continuous powder stream is transmitted through a nozzle and is split into two streams, one of which is applied to the fibrous substrate and the other is recirculated back to the feeding device.

WO 92/19198 discloses a device for applying a discrete layer of superabsorbent particles on a moving fibrous web, wherein a particle dispenser dispenses superabsorbent particles continuously over a movable belt provided with a pattern of holes, said belt is arranged at a short distance above and moves over the fibrous web, so that the superabsorbent particles are applied to the fibrous web in a pattern corresponding to the pattern of holes in the belt.

Development is now moving towards very thin absorbent structures, which means that a high content of superabsorbent material is required, in order to provide the necessary absorption capacity. It also requires a high manufacturing accuracy in order for the absorbent products to function in the intended manner. The demands of the consumers for a uniform quality and a better functioning in terms of leakage security, fit and comfort are also increasing. Moreover, the requirements for an improved performance and an increased price pressure due to a hard competition result in that the speed of the manufacturing process has to be increased.

An increased manufacturing speed results in that more exact conditions are required in connection with the forming of the absorbent structures contained in the absorbent articles. In combination with the demands for thinner products, this results in that known manufacturing methods are not functioning satisfactorily in all aspects.

OBJECTS AND SUMMARY

One problem to be solved by the present invention is to provide a method and a device for making thin absorbent structures containing high amounts of superabsorbent particulate material, which can be made in high manufacturing speeds and with a uniform quality.

This has according to an embodiment of the invention been achieved by a process in which at least one layer of fibrous material and at least one layer of particulate material are deposited in consecutive steps on a moving foraminous support to form layers on top of each other, wherein an airborn stream of particulate material is fed to an applicator chamber in a first feed direction at a high speed, usually between 25 and 40 m/s, said applicator chamber having an outlet opening located adjacent said foraminous support and the airborn stream of particulate material when entering said applicator chamber is allowed to expand and to hit a wall portion in said applicator chamber which is oriented at an angle between 90 and 125°, preferably between 100 and 120°, to said first flow direction, whereby the airborn stream of particulate material is forced to change flow direction to a second flow direction, resulting in a considerable reduction of speed of the airborn stream of particulate material as it exits the outlet opening of the applicator chamber.

In one embodiment of the invention the airborn stream of particulate material is applied on top of a layer of fibrous material deposited on said foraminous support. The particulate material is preferably a superabsorbent material.

According to one embodiment at least two layers of particulate material are applied on said foraminous support and a layer of fibrous material is applied between said layers of particulate material.

According to a further embodiment the particulate material is supplied intermittently to said foraminous support. In one embodiment of the invention the layer of fibrous material is in the form of separate web portions and the feed of said separate web portions on the foraminous support is synchronized with the intermittent supply of the particulate material onto the foraminous support.

With an embodiment of the invention a variety of thicknesses of layers of particulate material can be formed, from very thin layers having a basis weight of from 50 g/m$^2$, up to relatively thick layers having a basis weight up to 600 g/m$^2$. Preferably the basis weight of each layer of particulate material is between 80 and 250 g/m$^2$. The method also allows the particulate material to be deposited on thin fibrous layers, having a basis weight down to 30 g/m$^2$, without destroying said fibrous layers. Generally the basis weight of each fibrous layer is between 30 and 500 g/m$^2$, preferably between 50 and 80 g/m$^2$.

According to one embodiment the layer(s) of fibrous material is formed on a mat-forming wheel arranged adjacent said foraminous support and transferred to the foraminous support from the mat-forming wheel.

It is further encompassed by an embodiment of the invention that said airborn stream of particulate material contains a certain amount of fibrous material, and/or that the layer of fibrous material contains a certain amount of particulate material.

An embodiment of the invention also includes a device for forming a composite web containing at least one layer of particulate material and at least one layer of fibrous material, said web being intended for use as an absorbent structure in absorbent articles, such as diapers, pant diapers, incontinence products, sanitary napkins and the like, said device comprising means for depositing at least one layer of fibrous material and means for depositing at least one layer of particulate material in consecutive steps on a moving foraminous support to form layers on top of each other, wherein said device comprises at least one conveying means for feeding an airborn stream of particulate material in a first feeding direction at a high speed of at least about 25 m/s to an applicator chamber, said applicator chamber having an outlet opening located adjacent said foraminous support, and having a cross sectional area that increases towards said outlet opening, so that the airborn stream of particulate material when entering said applicator chamber is allowed to expand, said applicator chamber further having at least one curved or angled wall portion positioned at an angle between about 90 and about 125°, preferably between 100 and 120°, to said first flow direction, so as to cause said airborn stream of particulate material to hit said wall portion and change flow direction to a second flow direction, resulting in a considerable reduction of speed of the airborn stream of particulate material as it exits the outlet opening of the applicator chamber.

In one embodiment of the invention the applicator chamber has an inlet portion and an outlet portion interconnected by said curved or angled wall portion, the inlet portion as well as the outlet portion having an expanding cross sectional area, the inlet portion connects to and is oriented in substantially the same direction as the conveying means and the outlet portion is oriented in a direction that is at an angle between about 90 and about 125°, preferably between 100 and 120°, to the orientation of the conveying means and the inlet portion.

In one embodiment the device comprises at least two applicator chambers arranged after each other along said foraminous support and that means for depositing fibrous material are arranged along said foraminous support before and intermediate said at least two applicator chambers.

In a further embodiment the device comprises means for depositing fibrous material arranged along said foraminous support after said at least two applicator chambers.

According to one embodiment said means for depositing fibrous material comprises a mat-forming wheel arranged adjacent said foraminous support and arranged to transfer a layer of fibrous material formed on said mat-forming wheel to the foraminous support.

In one embodiment of the invention the matforming wheel is arranged to form a continuous fibrous layer. In another aspect the matforming wheel comprises as plurality of discrete moulds arranged to form a plurality of separate fibrous web portions.

According to one embodiment the means for depositing the particulate material is provided with means for intermittent supply of said particulate material to said applicator chamber. Said means for intermittent supply of the particulate material may be synchronized with the feed of said separate fibrous web portions on the foraminous support.

An embodiment of the invention further refers to an absorbent structure comprising a composite web structure containing fibrous material and particulate superabsorbent material, wherein it comprises at least one layer of superabsorbent particles arranged between discrete layers of fibrous material, said composite web structure has been made by the method according to the invention.

In one embodiment the composite web comprises at least two layers of superabsorbent particles arranged between discrete layers of fibrous material.

According to a further embodiment the absorbent structure comprises at least 50% by weight of particulate superabsorbent material. In further aspects of the invention is comprises at least 60% and preferably at least 70% by weight of particulate superabsorbent material.

BRIEF DESCRIPTION OF THE DRAWINGS

The invention will below be closer described with reference to some embodiments shown in the accompanying drawings.

DETAILED DESCRIPTION OF THE PREFERRED EMBODIMENTS

The following description will be made with reference to forming a layer of superabsorbent particulate material within a composite fibrous web. However it should be understood that the invention can be used to form layers of other particulate materials within a composite fibrous web. The composite web can be used as an absorbent structure in absorbent articles, such as diapers, pant diapers, incontinence products, sanitary napkins and the like.

Superabsorbent polymers are materials having the ability to absorb water or bodily fluids many times their own weight, usually 20 times or more. Examples of superabsorbent polymers are alkali metal salts of polyacrylic acid, polyacrylates, poly acrylic acid, polyacryl amides, derivatives of cellulose such as carboxy methyl cellulose, starch and starch derivatives, acrylic acid grafted starch etc. Particles of superabsorbent material may be in the form of granules, flakes of fibers, wherein granules are most commonly occurring. The particle size for granules typically measures about 50-1000 µm in diameter, preferably between 200-800 µm.

Figure 1:
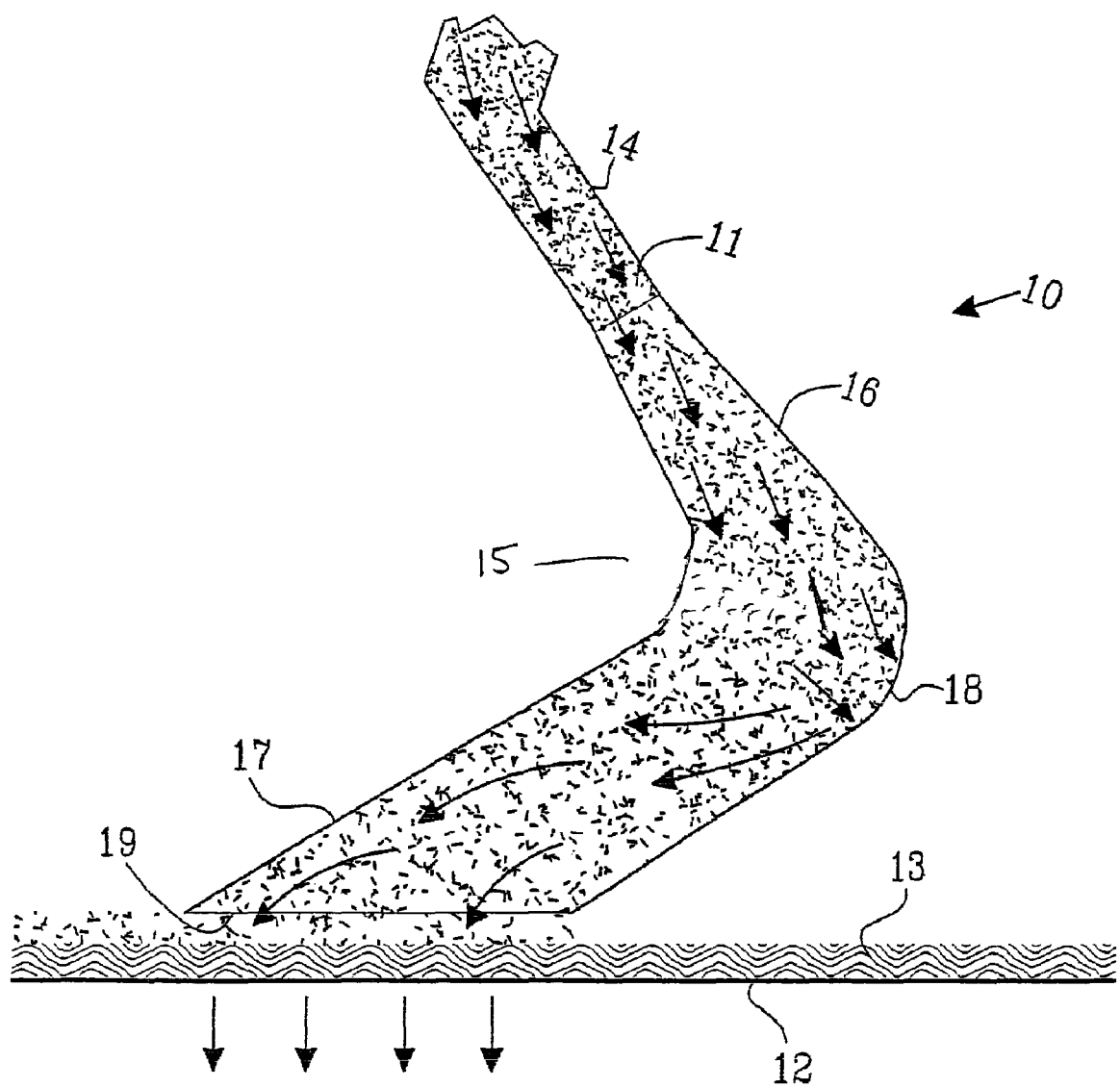
FIG. 1 shows a schematic longitudinal section through a device for depositing a superabsorbent particulate material on a moving foraminous support.

FIG. 1 illustrates schematically a device 10 for depositing particulate material, especially superabsorbent material 11, onto a moving foraminous support 12 having a suction box (not shown) mounted thereunder. The foraminous support normally carries a fibrous web 13 onto which the superabsorbent particles are deposited. The device 10 comprises a conveying conduit 14 for transporting an airborn stream of the superabsorbent material 11 into an applicator chamber 15. The superabsorbent material is delivered to the conveying conduit from a dosing unit (not shown) by any suitable method known to the person skilled in the art and is either delivered as a continuous flow or as an intermittent flow. One dosing unit may deliver superabsorbent material to one or more applicator chambers 15.

The velocity of the superabsorbent material conveyed through the conduit is high, about 25-40 m/s, in order to provide an even distribution of the superabsorbent particles in the air stream. However it is not desired that the velocity of the superabsorbent particles when hitting the fibrous web 13 supported by the foraminous support 12 is especially high, since the superabsorbent particles may then penetrate through the fibrous web. A certain penetration of the superabsorbent particles into the fibrous web can be accepted, but it is usually not desired that the particles penetrate the web completely.

The applicator chamber 15 has an inlet portion 16 and an outlet portion 17 and a curved or angled wall portion 18 therebetween. The inlet portion 16 as well as the outlet portion 17 both have an expanding cross sectional area in the transport direction of the particulate superabsorbent material. The inlet portion 16 connects to and is oriented in substantially the same direction as the conveying conduit 14. The outlet portion 17 is oriented in a direction that is positioned at an angle between about 90 and about 125°, preferably between 100 and 120°, to the orientation of the conveying conduit 14 and the inlet portion 16. The orientation of the outlet portion 17 is further such that its rear wall portion, as seen in the feeding direction of the foraminous support 12, makes an angle α with said foraminous support of between 20 and 80°, preferably between 40 and 70°. An effective reduction of velocity of the superabsorbent particles is achieved by the expansion of the air born stream as it enters the applicator chamber 15 and by hitting the curved or angled wall portion 18. This means that the air born stream of superabsorbent particles is forced to change its direction of flow before exiting the outlet opening 19, which will lead to a very effective speed reduction. The superabsorbent particles will then be deposited on the fibrous web 13 carried by the foraminous support 12 at a speed that is low enough not to destroy the fibrous web 13 and that will provide an even layer of superabsorbent particles.

Figure 2:
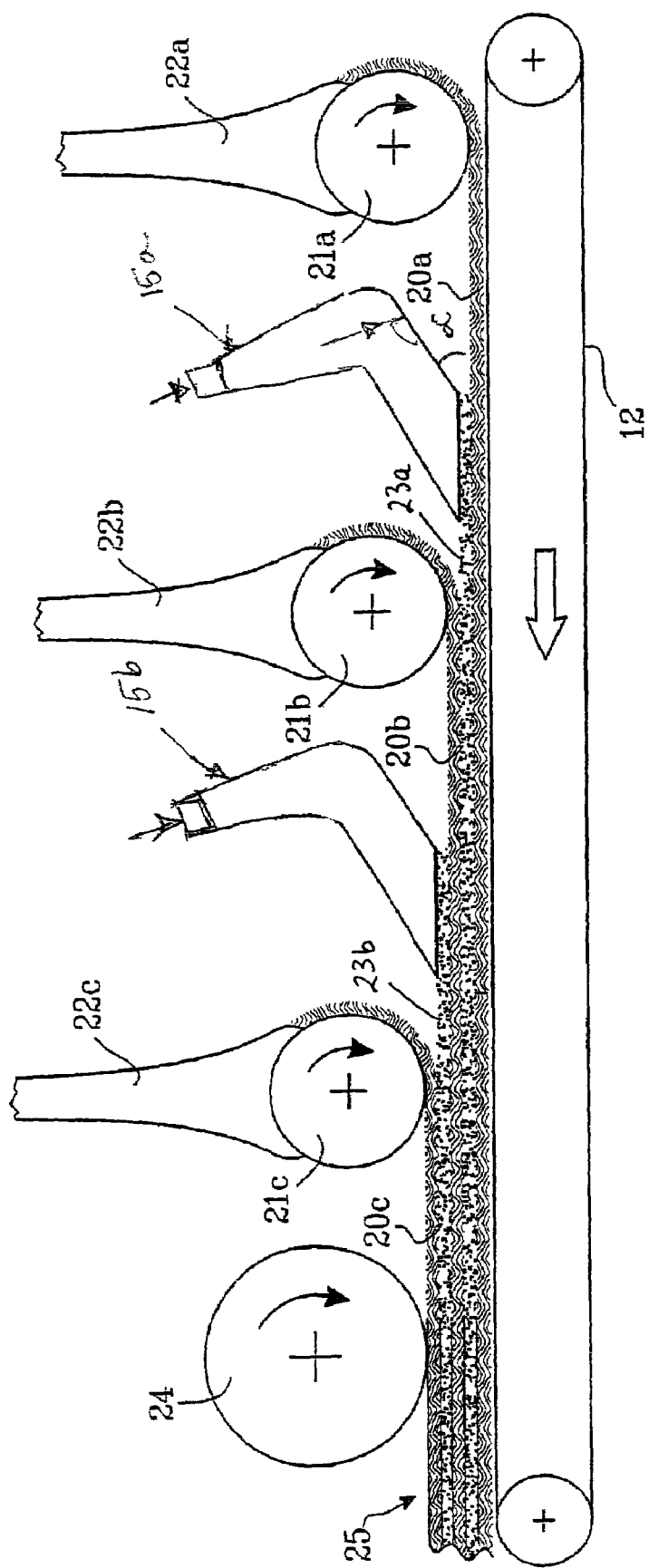
FIG. 2 is a schematic view of an embodiment of a method and device according to the invention.

FIG. 2 shows a schematic side view of a process for making a layered structure of three fibrous layers and two layers of superabsorbent particles. A first layer 20a of fibers is formed on a first matforming wheel 21a and is separated from and conveyed onto a foraminous support 12 having a suction box mounted thereunder. The fibers, for example cellulosic fluff pulp, are delivered in the form of an airborn stream from a pulp mill (not shown) to a matforming hood 22a arranged adjacent the matforming wheel 21a. Inside the matforming wheel a negative pressure prevails opposite the matforming hood 22a, so that the fibers adhere to the air pervious surface of the matforming wheel. Adjacent the foraminous support 12 the pressure in the matforming wheel 21a is slightly positive or at least there is a pressure difference between the underside of the foraminous support and the inside of the matforming wheel such that the fibrous web 20a is easily separated from the matforming wheel 21a and transferred to the foraminous support 12.

A first layer 23a of superabsorbent particles is then deposited on top of the first fibrous layer 20a by means of a first applicator chamber 15a according to the invention as described above.

A second fibrous layer 20b is applied on top of the first superabsorbent layer 23a by means of a second matforming wheel 21b which is similar to the first matforming wheel 21a.

A second layer 23b of superabsorbent particles is deposited on top of the second fibrous layer 20b by means of a second applicator chamber 15b according to the invention as described above.

Finally a third fibrous layer 20c is applied on top of the second superabsorbent layer 23b by means of a third matforming wheel 21c which is similar to the first and second matforming wheels.

In certain embodiments the airborn stream of fibers supplied to any of the matforming wheels may comprise a certain amount of superabsorbent material. In a corresponding manner the airborn stream of superabsorbent particles may contain a certain amount of fibrous material, for example cellulosic fluff pulp.

The composite web is subsequently compressed in a compression device 24 before it is removed from the foraminous support 12. In the arrangement shown in FIG. 2 a continuous composite web 25 is formed. This can in conjunction with or after compression be cut into suitable dimensions and shapes to form individual absorbent structures in absorbent articles.

It is of course possible to vary the number of matforming wheels 21 and superabsorbent applicator chambers 15 to any desired number depending on how many layers the composite web should comprise. It is often desired that the first and second layer forms is a fibrous layer, so that the particulate superabsorbent material is held in place between fibrous layers.

Figure 3:
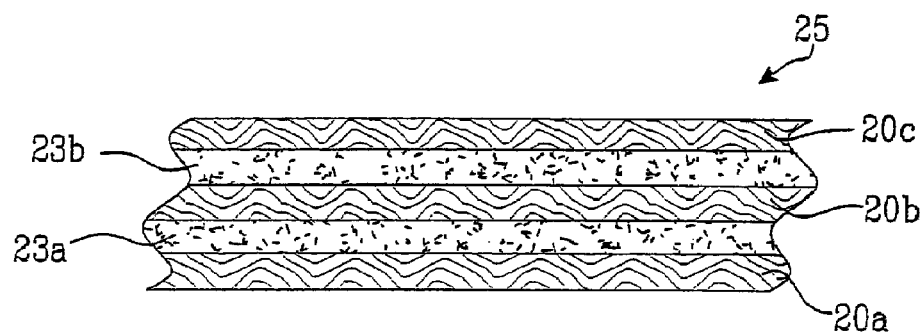
FIG. 3 is a schematic cross sectional view of a composite web produced according to an embodiment of the invention.

FIG. 3 shows a schematic cross section of a composite web 25 produced by the device and method disclosed in FIG. 2.

With the method and the device shown in FIG. 2 composite webs 25 of fibrous material and superabsorbent material in a layered configuration can be produced at high speeds and with a uniform quality and basis weights of the individual layers formed. The basis weight variation can be reduced considerably as compared to other manufacturing processes. Also the quality of the layers formed is very high and due to the effective speed reduction of the superabsorbent particles in the applicator chamber 15 an undesired penetration of particles through the underlying fibrous layer is avoided or at least considerably reduced. This means that thinner layers of fibers can be used in the individual fibrous layers. This in turn leads to that an increase of the proportion of superabsorbent material relative to fibers is possible.

The basis weights of the individual fibrous layers can vary between 30 and 500 g/m$^2$, preferably between 50 and 80 g/m$^2$ and the basis weights of the individual superabsorbent layers can vary between 50 and 600 g/m$^2$, preferably between 80 and 250 g/m$^2$. Thus absorbent structures comprising a plurality of very thin layers can be produced. When speaking about "layers" it is emphasized that the layers are more or less integrated so as to form a composite web. The proportion between fibers and superabsorbent particles can be controlled and varied between wide ranges, but the content of superabsorbent particles is preferably at least 50% by weight calculated on the total weight of the composite web. It may for certain product applications be desired to have at least 60% and preferably at least 70% by weight superabsorbent material. The composite web 25 is preferably compressed to a high density, preferably between 0.2 and 1.0 g/cm$^3$ and more preferably between 0.3 and 0.6 g/cm$^3$.

Furthermore the composite web 25 can optionally be compressed with different degrees or patterns of compression in different areas.

Figure 4:
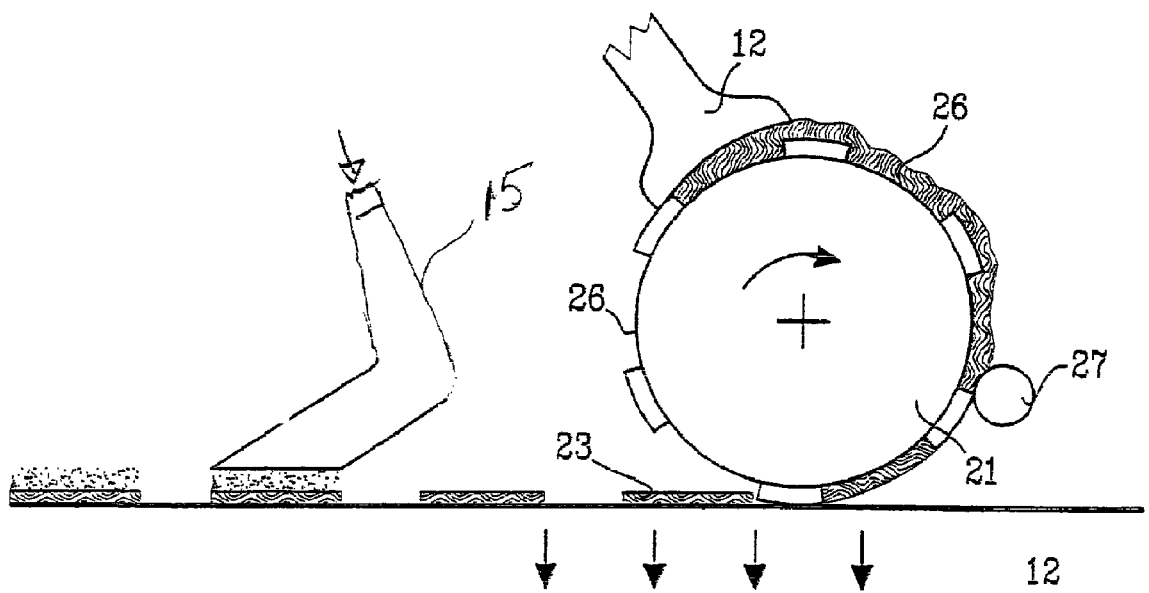
FIG. 4 is a schematic view of an alternative embodiment of the method and a device according to an embodiment of the invention.

In FIG. 4 there is disclosed an alternative embodiment of a part of a device for making discrete absorbent structures. The matforming wheel 21 is provided with a plurality of moulds 26 along its periphery, which have the correct size and shape to make a part of an absorbent structure in an absorbent article. Fibrous material is applied in the moulds 26 from a matforming hood 22 and excess of fibrous material deposited between the moulds is removed by a milling cutter 27. The portions of fibrous material 20 formed on the matforming wheel are separated therefrom and transferred to a foraminous support 12 in the same manner as disclosed above with reference to FIG. 2. An applicator chamber 15 for superabsorbent material of the same type as disclosed above is provided to apply a layer of superabsorbent material on top of the fibrous layer portions 23.

It is in this preferred embodiment that the superabsorbent material is applied intermittently only on top of the fibrous layer portions 23 and not between them. This can be provided either by supplying the superabsorbent material to the applicator chamber 15 with a pulsating flow, which is synchronized with the matforming wheel 21, or alternatively by dispensing the superabsorbent particles continuously over a movable belt provided with a pattern of holes, said belt is arranged at a short distance above and moves over foraminous support as disclosed in WO 92/19198, so that the superabsorbent particles are applied in a pattern corresponding to the pattern of holes in the belt. This pattern of holes corresponds to the fibrous layer portions 23 and the belt is synchronized with the matforming wheel, so that the superabsorbent particles are applied only on the fibrous layer portions 23 and not between them. A plurality of matforming wheels 21 and superabosrbent applicator chambers 15 may be arranged in the same manner as disclosed in FIG. 2 and described above.

Figure 5:
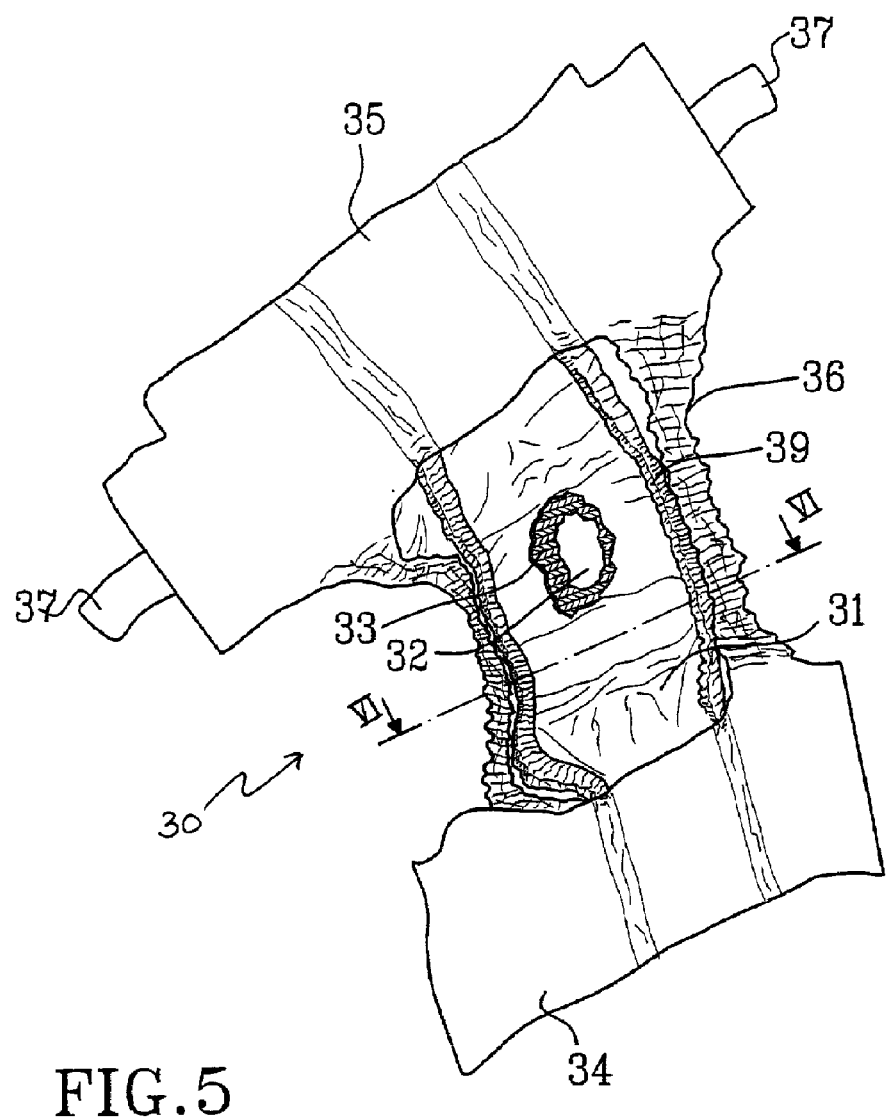
FIG. 5 shows a plan view of an absorbent article in the form of a diaper.

The following description refers to an embodiment of an absorbent article according to the invention, which is not limited to the below described embodiment. In FIG. 5 a planar view is shown of an absorbent article 30. The term "absorbent article" refers to products that are placed against the skin of the wearer to absorb and contain body exudates, like urine, faeces and menstrual fluid. The invention mainly refers to disposable absorbent articles, which means articles that are not intended to be laundered or otherwise restored or reused as an absorbent article after use. Examples of disposable absorbent articles include feminine hygiene products such as sanitary napkins, panty liners and sanitary panties; diapers and pant diapers for infants and incontinent adults; incontinence pads; diaper inserts and the like.

Figure 6:
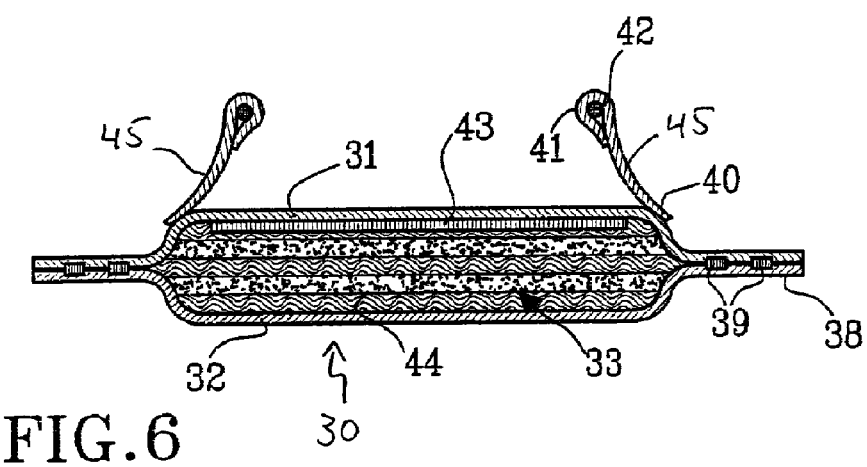
FIG. 6 is a cross-section through the absorbent article according to FIG. 5.

FIGS. 5 and 6 show an embodiment of a diaper 30 for an infant or an incontinent adult, said diaper typically comprises a chassis comprising a liquid permeable topsheet 31, a liquid impermeable backsheet 32 and an absorbent body 33 enclosed therebetween. The liquid permeable topsheet 31 can consist of a nonwoven material, e g spunbonded, meltblown, carded, hydroentangled, wetlaid etc. Suitable nonwoven materials can be composed of natural fibers, such as woodpulp or cotton fibers, manmade fibers, such as polyester, polyethylene, polypropylene, viscose etc. or from a mixture of natural and manmade fibers. The topsheet material may further be composed of a layer of continuous fibers, so called tow, which may be bonded to each other in a bonding pattern, but where the fibers otherwise are substantially unbonded to each other, as e.g. disclosed in EP-A-1 035 818. Further examples of topsheet materials are porous foams, apertured plastic films etc. The materials suited as topsheet materials should be soft and non-irritating to the skin and be readily penetrated by body fluid, e g urine or menstrual fluid.

The liquid impermeable backsheet 32 may consist of a thin plastic film, e.g. a polyethylene or polypropylene film, a nonwoven material coated with a liquid impervious material, a hydrophobic nonwoven material, which resists liquid penetration or laminates of plastic films and nonwoven materials. The backsheet material may be breathable so as to allow vapour to escape from the absorbent core, while still preventing liquids from passing through the backsheet material.

The topsheet 31 and the backsheet material 32 have a somewhat greater extension in the plane than the absorbent body 33 and extends outside the edges thereof. The layers 31 and 32 are connected to each other within the projecting portions thereof, e g by gluing or welding by heat or ultrasonic. The topsheet and/or the backsheet may further be attached to the absorbent core by any method known in the art, such as adhesive, heatbonding etc. The absorbent core may also be unattached to the topsheet and/or the backsheet.

The absorbent core 33 comprises a composite web as disclosed above. It may also comprise other layers, such as liquid acquisition layers and/or liquid distribution layers. The size and absorbent capacity of the absorbent core may be varied to be suited for different uses such as baby diapers, adult incontinence diapers and pads, pant diapers, panty liners, sanitary napkins etc.

The diaper disclosed in FIG. 5 is intended to enclose the lower part of the wearer's trunk like a pair of absorbent pants. It comprises a front portion 34 intended during use to be worn on the front part of the user's body, a rear portion 35 intended during use to be worn on the rear part of the user's body, and a more narrow crotch portion 36 located between the front and rear portions and which is intended to be worn in the crotch part of the user between the legs. The rear portion 35 is provided with a pair of adhesive tape tabs 37 or other type of attachment means such as hook-and-loop type fasteners.

The diaper comprises elasticised side flaps 38 forming leg openings. Elastification is provided by elastic members 39 secured between the topsheet and backsheet in the side flap region 38. The diaper disclosed in FIG. 5 and 6 further comprises elastic barrier flaps 45 having a proximal edge 40 and a distal edge 41 and elastic member 42 spacing the distal edge 41 away from the topsheet. These barrier flaps 45 form leakage barriers and are at their proximal edges 40 secured to the topsheet 31 close to the lateral edges of the absorbent core 33 either in the area of the side flaps 38 or above the absorbent core 33.

The diaper may further comprise elasticised waist feature in the form of elastic members extending in the transverse direction of the article in the waist portion thereof.

The absorbent structure 33 comprises a liquid acquisition layer 43, which is intended to be able to rapidly receive large amounts of liquid and to temporarily hold and distribute liquid before it is transferred to a storage layer 44, which is intended to be able to absorb and store large amounts of liquid. The acquisition layer 43 should have the capability of quickly receiving large amounts of liquids and may comprise a porous fibrous layer of wet resilient fibers, such as synthetic fibers, or polymeric foam materials. It may further be composed of tow fibers, which may be bonded to each other in a bonding pattern, as e.g. disclosed in EP-A-1 035 818. The acquisition layer 43 may also be composed of a superabsorbent foam material or a fibrous layer having super absorbent particles or a super absorbent coating bound to the fibrous layer.

The storage layer 44 comprises an absorbent structure in the form of a composite web 25 as disclosed above. The storage layer 44 preferably comprises three fibrous layers and two superabsorbent layers. According to an embodiment of the invention at least two fibrous layers, preferably at least three, and at least two superabsorbent layers are provided in the composite web constituting the storage layer 44. It is understood that the storage layer can comprise any optional number of layers in addition thereto. The basis weights of the layers comprised in the composite web as well as the proportion of superabsorbent material are preferably as disclosed above.

In an alternative embodiment the storage layer 44 is arranged closest to the topsheet and the acquisition layer 43 beneath the storage layer, wherein the storage layer optionally is provided with apertures or recesses through which the liquid rapidly can penetrate and reach the underlying acquisition/distribution layer, which distributes the liquid before it is absorbed back into the storage layer. An additional storage layer may optionally be arranged below the acquisition/distribution layer. Such an absorbent structure is disclosed in Swedish patent application no. SE 0300878-6. At least one of the storage layers is in the form of a composite web 25 as disclosed above.

It is however understood that the diaper described above and shown in the drawings only represents a non-limiting examples and that the present invention is not limited thereto, but can be used in any type of absorbent articles as defined above.

Although only preferred embodiments are specifically illustrated and described herein, it will be appreciated that many modifications and variations of the present invention are possible in light of the above teachings and within the purview of the appended claims without departing from the spirit and intended scope of the invention.

What is claimed is:

1. A method of forming a composite web structure containing at least one layer of particulate material and at least one layer of fibrous material, said web structure being adapted for use as an absorbent structure in an absorbent article, the method comprising:
   depositing the at least one layer of fibrous material and the at least one layer of particulate material in consecutive steps on a moving foraminous support to form layers on top of each other,
   feeding an airborn stream of particulate material to an applicator chamber in a first flow direction at a high speed of about 25 m/s or higher, said applicator chamber having an outlet opening located adjacent to said foraminous support and that the airborn stream of particulate material when entering said applicator chamber is allowed to expand and to hit a wall portion in said applicator chamber which is oriented at an angle between about 90 and about 125° to said first flow direction, whereby the airborn stream of particulate material is forced to change flow direction to a second flow direction, resulting in a reduction of speed of the airborn stream of particulate material as it exits an outlet opening of the applicator chamber, wherein the airborn stream of particulate material that exits the outlet opening of the applicator chamber is directly deposited on the moving foraminous support.

2. The method according to claim 1, wherein the airborn stream of particulate material is applied on top of a layer of fibrous material deposited on said foraminous support.

3. The method according to claim 1, wherein said particulate material is a superabsorbent material.

4. The method according to claim 1, wherein applying at least two layers of particulate material on said foraminous support and applying a layer of fibrous material between said layers of particulate material.

5. The method according to claim 1, wherein the particulate material is supplied intermittently to said foraminous support.

6. The method according to claim 5, wherein the layer of fibrous material is in the form of separate web portions and a feed of said separate web portions on the foraminous support is synchronized with the intermittent supply of the particulate material onto the foraminous support.

7. The method according to claim 1, wherein basis weight of each layer of particulate material is between 50 and 600 g/m2.

8. The method according to claim 7, wherein the basis weight is between 80 and 250 g/m$^2$.

9. The method according to claim 1, wherein the basis weight of each layer of fibrous material is between 30 and 500 g/m2.

10. The method according to claim 9, wherein the basis weight is between 50 and 80 g/m$^2$.

11. The method according to claim 1, wherein the at least one layer of fibrous material is formed on a mat-forming wheel arranged adjacent said foraminous support and transferred to the foraminous support from the mat-forming wheel.

12. The method according to claim 1, wherein said airborn stream of particulate material contains an amount of fibrous material.

13. The method according to claim 1, wherein the layer of fibrous material contains an amount of particulate material.

14. The method according to claim 1, wherein the absorbent article is a diaper, pant diaper, incontinence product, or sanitary napkin.

15. The method according to claim 1, wherein the angle is between 100° and 120°.

16. An absorbent structure comprising a composite web structure containing fibrous material and particulate superabsorbent material made according to the method of claim 1, wherein the composite web comprises at least one discrete layer of superabsorbent particles arranged between discrete layers of fibrous material, each of said layers of superabsorbent particles having a basis weight between 50 and 600 g/m$^2$ and each of said layers of fibrous material having a basis weight of between 30 and 500 g/m$^2$.

17. The absorbent structure according to claim 16, wherein the composite web comprises at least two discrete layers of superabsorbent particles.

18. The absorbent structure according to claim 16, wherein the composite web comprises at least 50% by weight of particulate superabsorbent material.

19. The absorbent structure according to claim 18, wherein the composite web comprises at least 60% by weight of particulate superabsorbent material.

20. The absorbent structure according to claim 19, wherein the composite web comprises at least 70% by weight of particulate superabsorbent material.

21. The absorbent article that comprises an absorbent structure as defined in claim 16.

22. The absorbent structure according to claim 16, wherein each of the layers of superabsorbent particles has a basis weight between 80 and 250 g/m$^2$ and each of the layers of fibrous material has a basis weight of between 50 and 80 g/m$^2$.

* * * * *